United States Patent [19]

Greenquist

[11] Patent Number: 4,772,550
[45] Date of Patent: Sep. 20, 1988

[54] HETEROGENEOUS SPECIFIC BINDING ASSAY EMPLOYING AN AGGREGATABLE BINDING REAGENT

[75] Inventor: Alfred C. Greenquist, Elkhart, Ind.

[73] Assignee: Miles Inc., Elkhart, Ind.

[21] Appl. No.: 827,967

[22] Filed: Feb. 10, 1986

[51] Int. Cl.⁴ .................. G01N 53/00; G01N 33/546; G01N 33/551

[52] U.S. Cl. ....................................... 435/7; 435/288; 435/805; 435/810; 436/503; 436/524; 436/529; 436/533; 436/534; 436/539; 436/808; 436/810; 436/824

[58] Field of Search .................... 435/7, 288, 805, 810; 436/503, 524, 529, 533, 534, 539, 808, 810, 824

[56] References Cited

U.S. PATENT DOCUMENTS

| | | | |
|---|---|---|---|
| 4,033,722 | 7/1977 | Lindstrom | 436/539 |
| 4,278,653 | 7/1981 | Harris et al. | 436/808 X |
| 4,298,685 | 11/1981 | Parikh et al. | 436/503 |
| 4,427,781 | 1/1984 | Masson et al. | 436/534 X |
| 4,490,465 | 12/1984 | Limbach et al. | 435/805 X |
| 4,522,922 | 6/1985 | Carro et al. | 436/808 X |
| 4,530,900 | 7/1985 | Marshall | 436/539 X |
| 4,547,466 | 10/1985 | Turanchik et al. | 436/534 X |

*Primary Examiner*—Sidney Marantz
*Assistant Examiner*—Richard Wagner
*Attorney, Agent, or Firm*—Daniel W. Collins

[57] ABSTRACT

A heterogeneous specific binding assay method for determining the amount of a suspected analyte in an aqueous test medium wherein a reaction mixture is formed by combining the test medium with assay reagents including a labeled reagent, an immobilizable component, and a binding substance which causes the immobilizable component to precipitate. Free and bound species of the labeled reagent are formed as a function of the amount of the analyte in the test medium. One of the free and bound species of the labeled reagent is immobilized by binding of the immobilizable component with the binding substance. The immobilized labeled reagent is seperated from labeled reagent which has not been immobilized, and the amount of label in the labeled reagent in one of the separated fractions is determined and related to the amount of analyte in the test medium. The improvement provided is the use of an immobilizable component comprising a water dispersible, aggregatable reagent comprising a binding partner for the one of the free and bound species to be immobilized and a first binding substance which upon binding of a second binding substance forms a precipitated complex of the aggregatable reagent.

39 Claims, 3 Drawing Sheets

COMPETITIVE BINDING

SANDWICH TECHNIQUE

IMMUNOMETRIC TECHNIQUE

HETEROGENEOUS SPECIFIC BINDING ASSAY EMPLOYING AN AGGREGATABLE BINDING REAGENT

BACKGROUND OF THE INVENTION

1. Field of the Invention

The present invention relates to specific binding assays (e.g., immunoassays) which are useful for the determination of an analyte in a liquid test medium. In particular, the present invention relates to heterogeneous specific binding assays for the determination of the amount of suspected analyte in an aqueous test medium involving the formation and subsequent physical separation of "bound" and "free" forms of a labeled reagent from one another in order to complete the assay.

2. Description of the Prior Art

Heretofore, various binding assays using immobilized or immobilizable materials for the direct immobilization of one of the binding participants in a binding assay reaction, e.g., immobilized antigen or antibody, in order to accomplish the desired separation of the bound and free forms of a labeled reagent, have been proposed. In particular, a number of such binding assays have been described wherein an antibody to an antigen to be detected is bound to an immobilizing material such as the inner wall of a test tube or a plastic bead.

For example, in U.S. Pat. No. 4,243,749, a competitive binding assay is disclosed wherein a reaction is carried out in a test tube having a specific antibody to a hapten under determination insolubilized or immobilized on the inner wall of the test tube. The reaction includes a labeled hapten conjugate wherein the quantity of the labeled hapten conjugate which becomes bound to the test tube wall is inversely proportional to the amount of the hapten under determination.

Another of such binding assays is described by U.S. Pat. No. 4,230,683 which discloses a method employing a 6 mm polystyrene bead having antigen or antibody bound thereto wherein the antigen or antibody is reacted with a hapten-conjugated antibody to the antigen or antibody. The bound hapten-conjugated antibody is further reacted with labeled anti-hapten antibody in order to determine the amount of antigen or antibody in a test sample.

Still another of such binding assays is described by U.S. Pat. No. 4,228,237 which discloses a method for the detection and determination of ligands in a liquid medium using enzyme labeled avidin and a biotin labeled reagent in a specific binding process. In this method, the ligand to be detected is contacted with an insoluble phase containing a specific binding substance for the ligand.

In addition to the direct immobilization techniques heretofore described, indirect immobilization by marking or labeling a binding assay reaction participant to be immobilized with a first binding substance, and then adding an immobilized second binding substance, has been proposed.

For example, U.S. Pat. No. 4,298,685 discloses an enzyme immunoassay wherein a sample containing a biological substance under determination is mixed with antibodies to the biological substance tagged with biotin and with an enzyme-labeled form of the substance under assay. An immobilized form of avidin is then added wherein the avidin binds to the biotin-tagged antibody to immobilize the antibody-bound fraction of the enzyme-labeled reagent. Similarly, United Kingdom Patent Application No. GB 2,084,317A discloses an antigen-linked competitive enzyme immunoassay using avidin bound to a solid material and a biotin-labeled antigen.

Accordingly, it is an object of the present invention to provide a specific binding assay for the detection of an analyte in a liquid test medium that does not require centrifugation steps or similarly complex, cumbersome separation techniques as heretofore described to separate an immobilized complex from the reaction solution before the amount of analyte can be determined.

Further, it is an object of the present invention to provide an immobilizable component having more than one molecule of the binding partner under determination bound thereto so that a minimal amount of binding substance which precipitates the immobilizable component is needed.

Another object of the present invention is to provide an immobilizable component having an enhanced surface area or availability of a binding partner for a specific binding assay reaction.

It is still a further object of the present invention to provide a specific binding assay which can be performed within a reaction vessel without the need for additional rinsing or washing steps after the specific binding reaction has taken place and where only a small aliquot of a reaction solution is needed to determine the amount of analyte in the test medium.

SUMMARY OF THE INVENTION

The present invention provides a simplified, heterogeneous specific binding assay which can be adapted to detect a variety of biological substances in a liquid test medium and which can be performed with a minimal number of steps. The assay of the present invention is performed in a single reaction vessel without the need for centrifugation or similarly complex steps. A reaction mixture is formed by combining the test medium with assay reagents of the present invention which include (i) a labeled reagent, such as labeled anti-analyte, which forms free and bound species of the labeled reagent as a function of the amount of analyte in the test medium, and (ii) an immobilizable component which binds to one of the free or bound species of the labeled reagent, and thereby ultimately forms an immobilized labeled reagent whereby the immobilized labeled reagent can be separated from the labeled reagent which has not been immobilized.

The improvement of the present invention resides in the use of an immobilizable reagent which comprises a water dispersible, aggregatable support material having coupled thereto both a binding partner for the one of the free or bound species of the labeled reagent to be immobilized and a first binding substance. The immobilized labeled reagent is formed by adding a second binding substance to the reaction mixture wherein the second binding substance has a binding affinity for the first binding substance. In this manner, the second binding substance causes the support material to aggregate as a result of the binding of the first binding substance and the second binding substance and to thereby form one fraction containing a precipitated complex of the support material and a second fraction containing the labeled reagent which has not been immobilized. The amount of label in the labeled reagent in one of the fractions is determined and related to the amount of analyte in the test medium.

The present invention also provides for a test kit which includes a quantity of the labeled reagent, the immobilizable reagent, the specific binding substance for the immobilizable reagent, and optionally, an indicator which provides a detectable signal proportional to the amount of the analyte in the test medium.

DESCRIPTION OF THE PREFERRED EMBODIMENTS

The specific binding assay method of the present invention can be applied to conventional heterogeneous specific binding assay methods, such as radioimmunoassays and heterogeneous enzyme immunoassays. The assay reagents for performing such assays may take many different forms, but, in general, comprise (1) the analyte to be detected, (2) a specific binding partner for the analyte, and (3) a labeled reagent, which can be the same or different as the binding partner for the analyte. The assay reagents are generally combined simultaneously, or sequentially, wherein the labeled reagent becomes bound to its corresponding binding partner such that the extent of binding is a function of the amount of analyte present. Typically, the bound species and the free species are physically separated from each other and the amount of label present in either fraction thereof is determined by measuring the activity of the particular label being used.

The various methods available in the art for forming binding reaction systems can be followed in applying the method of the present invention. Such methods include those known as the competitive binding technique, the "sandwich" technique, and the immunometric technique. In all of these heterogeneous immunoassay systems, separation of the free and bound species of the labeled reagent is normally accomplished by immobilizing one of such species. Accordingly, the improved immobilization process of the present invention can be applied advantageously to such known systems.

Figure 1:
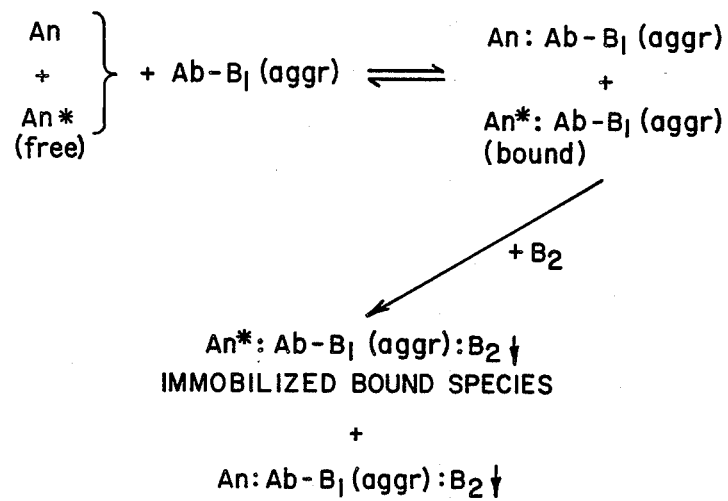
FIG. 1 is a diagramatical illustration of a conventional competitive binding reaction system as applied to the specific binding assay method of the present invention.

As applied to the present invention, the assay reagents which form the reaction mixture of the competitive binding technique include (1) the analyte being detected, (2) a labeled reagent, which is usually a labeled form of the analyte being detected or specific binding analog thereof, and (3) an immobilizable, aggregatable binding partner for the analyte being detected. In particular, referring to FIG. 1, the analyte being detected (represented as "An") and the labeled reagent (represented as "An*") compete for binding to the aggregatable binding partner [represented as "Ab-B$_1$ (aggr.)"], wherein any of the labeled reagent not becoming bound to the aggregatable binding partner being the "free" species and the labeled reagent bound to the aggregatable binding partner being the "bound" species [represented as "An*:Ab-B$_1$(aggr.)"].

As will be described in greater detail hereinafter, the aggregatable binding partner is associated with a first binding substance (represented as "B$_1$") having a binding affinity for a second binding substance (represented as "B$_2$"), such that when the second binding substance is added to the reaction mixture, the binding of the first binding substance with the second binding substance results in the "bound" species aggregating and thereby forming an immobilized precipitate (represented as "An*:Ab-B$_1$(aggr.):B$_2$") which can be readily separated from the "free" species.

Figure 2:
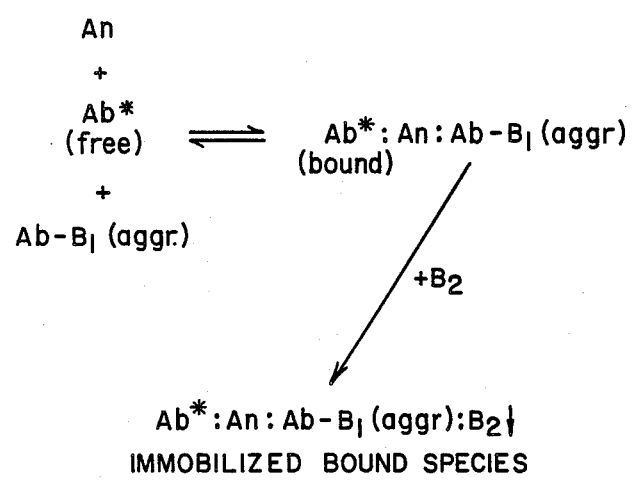
FIG. 2 is a diagramatical illustration of a conventional sandwich binding reaction system as applied to the specific binding assay method of the present invention.

The assay reagents used in the "sandwich" technique are similar to those reagents used in the competitive binding technique except for the nature of the labeled reagent. In particular, and referring now to FIG. 2, the labeled reagent is a labeled form of a second binding partner for the analyte being detected (represented as "Ab*") wherein a complex [represented as "Ab*:An:Ab-B$_1$(aggr.)"] comprising the first immobilizable binding partner [represented as "Ab-B$_1$(aggr.)"], the labeled second binding partner, and the analyte being detected (represented as "An") "sandwiched" therebetween is formed. The labeled second binding partner resulting in the complex shall be referred to as the "bound" species, and the labeled second binding partner not being a part of this "sandwiched" complex being the "free" species. When the second binding substance (represented as "B$_2$") is added to the reaction mixture, the "bound" species aggregates thereby becoming an immobilized precipitate (represented as "Ab*:An:Ab-B$_1$(aggr.):B$_2$") which is then separated from the "free" species.

Figure 3:
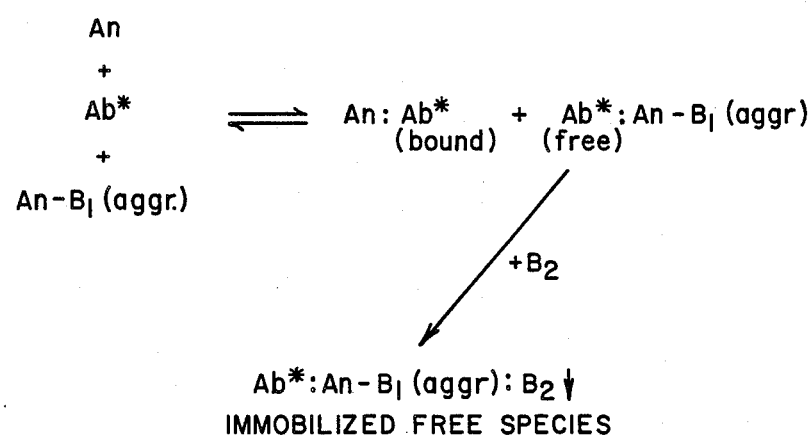
FIG. 3 is a diagramatical illustration of a conventional immunometric binding reaction system as applied to the specific binding assay method of the present invention.

Referring now to FIG. 3, under the immunometric technique, which is particularly preferred, the labeled reagent (represented as "Ab*") is a labeled form of an anti-analyte (e.g., an antibody or fragment thereof to the analyte being detected), and in addition to the analyte being detected, an immobilizable form of the analyte being detected [represented as "An-B$_1$(aggr.)"] is included in the binding reaction system. Generally, the labeled antibody (Ab*) binds either to the analyte being detected, or to the immobilizable form of the analyte being detected resulting in the formation of an immobilizable complex [represented as "Ab*:An-B$_1$(aggr.)"]. Here, the labeled antibody bound to analyte will be referred to as the "bound" species, and the immobilizable complex referred to as the "free" species. When the second binding substance (represented as "B$_2$") is added, the "free" species aggregates, thereby becoming an immobilized precipitate (represented as "Ab*:An-B$_1$(aggr.):B$_2$") which is then readily separated from the "bound" species.

Under the immunometric technique, as applied to the present invention, the labeled reagent, or labeled anti-analyte, is present in the reaction mixture in an exces amount relative to the estimated amount or concentration of suspected analyte in the test medium. Since the labeled reagent binds to the suspected analyte in the test medium, the excess amount of labeled reagent provides a sufficient number of binding partners for the suspected analyte in the test medium so that substantially all of the suspected analyte becomes bound by the labeled reagent, i.e., the "bound" species. It is to be appreciated that since the excess labeled reagent binds and thereby renders substantially all of the suspected analyte in the test medium detectable, an accurate and highly sensitive determination of the analyte can be made.

Similarly, the immobilizable form of the analyte being detected is present in the reaction mixture in an excess amount relative to the amount of the "free" form of the labeled anti-analyte which has not been bound by the labeled reagent and which remains as the "free" species in the reaction mixture. Accordingly, the excess amount of the immobilizable form of the analyte is at an excess amount such that a sufficient amount is present to bind substantially all of the "free" form of the laeled anti-analyte for the ultimate immobilization and separation of substantially all of the "free" species from the "bound" species. In this respect, in order to immobilize and thereby separate substantially all of the "free" species from the "bound" species, the second binding substance is added to the reaction mixture such that a sufficient amount of the second binding substance is present to form an aggregated, immobilized form of substantially all of the "free" species.

The use of excess amounts of reagents results in favorable kinetic and/or equilibrium advantages. In particular, excess amounts of reagents accelerate the kinetics of the binding reactions and thereby shift the equilibrium of the reaction to favor the formation of the bound species, even at low analyte concentrations. In contrast, a competitive assay format requires a limiting reagent antibody. In the immunometric format, the limiting reagent of the assay becomes the antigen (or hapten) itself. Accordingly, since the assay reagents are in excess amounts, the effect of variations in the concentration thereof on assay performance is less significant than that which is encountered in a conventional competitive assay format, and a margin of error in reagent additions is thereby permitted when made at least in excess amounts.

By shifting the equilibrium as heretofore described, it also becomes possible to reduce the level of unbound label which would affect the background signal and therefore the sensitity of the assay. Similarly, where the single antibody immunometric method is employed, the presence of non-specific binding does not create a background signal which would reduce the sensitivity of the assay, such as that encountered in sandwich-type immunoassays where two antibody binding reactions are involved and wherein the label bound to the immobilized phase is measured. The single antibody immunometric method also permits the application thereof to the detection of analytes having a single epitope, which is not feasible in a sandwich-type assay. Furthermore, where monoclonal-monovalent antibodies are employed in excess amounts in an assay, together with excess amounts of other assay reagents, the production of a linear dose response curve which facilitates the application of such assay format to a convenient calibration procedure is provided.

It should be appreciated that according to the teachings of the present invention, as will be described in greater detail hereinafter, manipulative techniques involving other orders of addition and other binding reaction formats can be developed for carrying out heterogeneous specific binding assays without departing from the teachings of the present invention.

Furthermore, the present invention can be applied to the detection of any analyte for which there is a specific binding partner and, conversely, to the detection of the capacity of a liquid medium to bind an analyte (usually due to the presence of a binding partner for the analyte in the medium). The analyte usually is a peptide, polypeptide, protein, carbohydrate, glycoprotein, steroid, nucleic acid or other organic molecule for which a specific binding partner exists in biological systems or can be synthesized. The analyte in functional terms, is usually selected from the group comprising antigens and antibodies thereto; haptens and antibodies thereto; and hormones, vitamins, metabolites and pharmacological agents, and their receptors and binding substances. Other analytes and/or binding pair components for which a specific binding partner exists include carbohydrates and lectins; metals and chelators; antibody, or fragment thereof, having an intact binding site for Protein A and Protein A; complementary single stranded oligo- and polynucleotide sequences; cofactor or prosthetic groups and apoprotein; effector molecules and receptor pairs; hydrophobic interactive pairs; enzyme cofactors and enzymes; polymeric acids and bases; dyes and protein binders; peptides and specific protein binders (e.g., ribonuclease, S-peptide and ribonuclease S protein); enzyme inhibitors (reversible and irreversible) and enzymes and the like. Usually, the analyte is an immunologically-active polypeptide or protein or carbohydrate or nucleic acid of molecular weight between 1,000 and 10,000,000, such as an antibody or antigenic polypeptide or protein, or a hapten of molecular weight between 100 and 1,500.

Still further, the labeled reagent will include a conventional detectable chemical group. Such detectable chemical group can be any material having a detectable physical or chemical property. Such materials have been well-developed in the field of immunoassays and in general any label useful in such methods can be applied to the present invention. Particularly useful are enzymatically active groups, such as enzymes (see Clin. Chem. (1976)22:1243), enzyme substrates (see U.S. Pat. No. 4,492,751), prosthetic groups or coenzymes (see U.S. Pat. Nos. 4,230,797 and 4,238,565), and enzyme inhibitors (see U.S. Pat. No. 4,134,792); spin labels; fluorescers (see Clin. Chem. (1979)25:353); chromophores; luminescers such as chemiluminescers and bioluminescers (see U.S. Pat. No. 4,380,580); specifically bindable ligands (e.g., biotin and haptens); electroactive species; and radioisotopes such as $^3H$, $^{35}S$, $^{32}P$, $^{125}I$, and $^{14}C$. Such labels and labeling pairs are detected on the basis of their own physical properties (e.g., fluorescers, chromophores and radioisotopes) or their reactive or binding properties (e.g., enzymes, substrates, coenzymes and inhibitors).

According to the teachings of the present invention, a binding assay reaction mixture is formed by combining the test medium with assay reagents which include a labeled reagent and an immobilizable reagent. The labeled reagent, preferably labeled anti-analyte, or, more specifically, a labeled monovalent antibody fragment of an antibody to the analyte being detected, forms free and bound species as a function of the amount of analyte in the test medium.

More specifically, the immobilizable reagent includes both a binding partner for the one of the free and bound species of the labeled reagent to be immobilized and a first binding substance whereby the immobilizable reagent will bind to one of the free and bound species of the labeled reagent. In this manner, an immobilizable labeled reagent is formed which is ultimately separated from the labeled reagent which has not been immobilized, as will be described in greater detail hereinafter.

The immobilized labeled reagent is formed by adding a second divalent or multivalent binding substance to the reaction mixture wherein the second binding substance has a binding affinity for the first binding substance. Accordingly, the second binding substance causes the support material to aggregate as a result of the intermolecular or interparticle binding of the first binding substance with the second binding substance wherein a fraction containing the non-immobilized labeled reagent and a fraction containing the precipitated support material complex comprising immobilized labeled reagent are formed.

Immobilizable Support Material

The immobilizable component or reagent of the present invention is a water dispersible, aggregatable support material which is adapted to aggregate or precipitate in the reaction solution thereby serving to separate the desired one of the bound and free species of the labeled reagent. The support material can either be a water soluble material, or a water suspensible, insoluble material.

In the case of a water suspensible, insoluble material, a polymeric microparticle, preferably a plastic bead, is used. The present inventor has found that the use of a macroparticle, such as the 6 mm bead disclosed by U.S. Pat. No. 4,230,683, presents the problem of a limited surface area, as well as the potential need for mixing. On the other hand, although increased surface and increased interaction with a support material can be accomplished with smaller beads, i.e., having a diameter less than 50 microns, there is still the need for a separation step which requires a centrifugation step to produce aggregation, particularly for particles less than 3 microns in diameter. Similarly, in the case of latex agglutination tests, a conventional analyte-antibody binding reaction is required to produce aggregation in order to achieve separation. Accordingly, the present invention overcomes this problem in a preferred embodiment by providing a plastic bead or microsphere having a diameter less than 50 microns and which includes a first binding substance of the present invention bound thereto which enhances the precipitatability of the bead upon the addition of an appropriate second binding substance so that the bound and free species can be separated without the need for centrifugation or similarly complex separation techniques.

Preferably, the nature of the beads employed according to the present invention are uniform latex particles which can be prepared by emulsion polymerization, or by suspension polymerization, resulting in particle sizes of less than 5 microns in diameter, or greater than 5 microns in diameter, respectively. In addition, particle sizes in the range from 2–20 microns in diameter can be effectively produced by "swollen emulsion polymerization" (Bangs, L., *Uniform Latex Particles*, Seragen, Inc., 1984).

Alternatively, other particle materials can be employed as aggregatable support materials and include particle materials made from polysaccharides such as crosslinked dextran or agarose, rubber, glass, nylon, and polyacrylate. Similarly, particles can be made from carboxylated polystyrene, polyvinyltoluene, or styrenebutadiamine copolymers, polyacrolein microspheres, polyurethane, poly (methyl methacrylate) particles, pollen particles, polyacrylamide, sporopollenin, polystyrene or polyvinylnapthalene cores surrounded by shells of polyglycidyl methacrylate, microcrystalline cellulose or combinations thereof, and the like.

Although the beads or microspheres employed according to the present invention can be prepared as described above, a broad range of microspheres from 0.38 to 20 microns in diameter are commercially available which have a multiplicity of functionalities, e.g., amino, carboxy, imino, or the like for covalently bonding reagents to the microsphere surface.

In the case of a water soluble material, an appropriate polymer is used. Similarly, the polymer includes a first binding substance of the present invention bound thereto which enhances the precipitatability of the polymer upon the addition of an appropriate second binding substance so that the bound and free species can be separated without the need for centrifugation or similarly complex separation techniques.

Preferably, such polymer material is a copolymer of polyamino acids, such as polyalanine, polylysine, and the like. Other polymers include dextrans and other polysaccharides, proteins, polynucleic acids (single stranded RNA or DNA), double stranded DNA, and polyethylene amine. Additional derivatizable polymers include polyvinyl alcohol, polyalyl alcohol, hydroxyethylcellulose, hydroxypropylcellulose and other natural and synthetic water-soluble polymers.

Specific examples of coupling of haptens and other biological molecules to agarose and polyacrylamides are described by Cuatrecasas in J. Biol. Chem. 245, p. 3059–3065 (1970) and W. B. Jacoby and M. Wilchek, Methods in Enzymology, Volume 34, Academic Press, New York, 1974. These methods can be used to covalently couple analytes (hapten) or the binding partner to polymers or the bead reagents. In addition, physical adsorption to insoluble carriers can be employed, for example, with glass and plastic beads.

It is to be appreciated that the binding partner, coupled to the immobilizable component, for the one of the free and bound species of the labeled reagent is preferably the analyte being detected, or a binding analog or a binding partner thereof. Accordingly, the immobilizable binding partner has a binding affinity for the labeled reagent whereby binding of the labeled reagent to the binding partner results in the formation of an immobilizable form of the desired one of the free and the bound species of the labeled reagent. In this manner, upon the precipitation of the immobilizable component, the desired one of the free and the bound species is separated from the other species as a result of the desired species being bound to the immobilizable component through the binding partner thereof.

Furthermore, it is also to be appreciated that one of the advantages of the immobilizable support material is that multiple binding partner molecules, as well as multiple molecules of the first binding substance, can be coupled thereto. As a result, multiple molecules of the desired one of the free and the bound species of the labeled reagent can be immobilized in order to permit the acceleration of the binding reactions as a result of a mass-action effect. Similarly, multiple molecules of the first binding substance coupled to the support material enhances the aggregation and precipitation of the support material complex by enabling one support material to be coupled to a number of support materials upon the addition of the second binding substance to the reaction solution.

Specific Binding Substances

As was heretofore described, the immobilizable component, or support material, of the present invention includes a first binding substance which is an essential part of the aggregation and subsequent precipitation of the support material complex upon the addition of the second binding substance to the reaction mixture. The second binding substance, having a divalent or multivalent binding affinity for the first binding substance, couples multiple support materials to each other as a result of the interaction between the first and second binding substances to thereby form a precipitable complex of the support material.

It will be appreciated that according to the teachings of the present invention, the nature of the first and second binding substances is not limited to any particular pair of binding substances. In this respect, a number of binding substance pairs can be used for the aggregation of the support material. Such binding substance pairs include biotin and avidin, hapten or antigen and antibody pairs, lectin and carbohydrate pairs, complimentary strands of single-stranded polynucleotides, polyacid and polybase pairs and the like. The selection of appropriate pairs enable the control, in part, of the rate of the aggregation reaction versus the specific binding (e.g., immunochemical) reaction of the labeled reagent binding to the binding partner coupled to the support material.

The second binding substance of the present invention can also be in either a soluble form or an insoluble form. In the case of the second binding substance being in an insoluble form, the second binding substance is insolubilized, or immobilized, on a solid support structure, such as a plastic bead or the inner wall of a polystyrene test tube. In this manner, removal of the aggregatable support material from the reaction mixture will be enhanced.

Test Kit

The assay reagents of the present invention are presented in a commercially packaged form as a composition or admixture where the compatibility of the reagents will allow, in a test device configuration, or as a test kit, i.e., a packaged combination of one or more containers holding the necessary reagents. Included in the assay reagents are the reagents appropriate for the binding reaction system desired. The assay reagents can further include other materials as are known to be useful in the assay from a user standpoint, such as buffers, diluents, standards and the like. Particularly preferred is a test kit for the heterogeneous specific binding assay of the present invention comprising (1) labeled anti-analyte, (2) a water dispersible, aggregatable reagent comprising a support material, such as plastic beads or a water soluble polymer, having a first binding substance and the analyte or a binding analog thereof coupled thereto, and (3) a second binding substance having a binding affinity for the particular first binding substance. The specific label used in the preferred test kit will depend on the technique followed, as described hereinabove. In a preferred embodiment, the label will be an enzyme and the test kit can additionally comprise an indicator which provides a color change in response to the activity of such enzyme. Such an indicator can be incorporated within a solid carrier matrix in the form of a test strip which can be immersed in the reaction mixture supernatant or to which an aliquot of the supernatant can be applied to provide a convenient means for detecting the non-immobilized species of the labeled reagent.

The present invention will now be illustrated, but is not intended to be limited, by the following examples:

EXAMPLE 1

Preparation of Enzyme Labeled Antibody

Ascites fluid containing an anti-digoxin antibody (~6 mg/mL) is diluted five-fold in 0.1M citrate buffer (pH 3.5) and incubated with a 1:50 (w/w) pepsin:antibody solution for 48 hours at 37° C. After concentration to ~5 mL by ultrafiltration over an Amicon PM30 membrane (Amicon Corp., Danvers, MA, USA), the sample is gel filtered on a Sephacryl ® S-300 (Pharmacia, Inc., Piscataway, NJ, USA) column (2.4×90 cm) and equilibrated with 10 mM sodium phosphate and 0.15M sodium chloride (pH 7.2) to isolate the F(ab')$_2$ fragment of the antibody. The antibody is reduced with 10 mM dithiothreitol and the protein peak is pooled after desalting on a G6PD polyacrylamide gel resin just before reaction with activated $\beta$-galactosidase. The $\beta$-galactosidase (type IX, Sigma Chemical Co., St. Louis, MO, USA) is dialyzed against 50 mM sodium phosphate (pH 7.4). A solution at 10 mg/mL is reacted with a heterobifunctional cross-linking agent, succinimidyl 4-(N-maleimidomethyl)cyclohexane-1-carboxylate, for two hours at room temperature, and this material is passed over a 1×60 cm G6PD column. The activated $\beta$-galactosidase is mixed with the antibody in a 1:1 ratio and reacted for twenty hours at 4° C. This material is concentrated approximately ten-fold by ultrafiltration over an Amicon PM30 membrane. The concentrate is passed over a 1.5×110 cm ACA 22 resin (LKB Instruments, Inc., Gaithersburg, MD, USA) to separate Fab-$\beta$-galactosidase from free antibody fragment (Fab) and from higher substituted oligomers of Fab and $\beta$-galactosidase. The principle enzyme/antibody fractions are pooled and passed over an affinity column containing immobilized ouabain. To prepare the immobilized ouabain column, ouabain is linked to bovine serum albumin similar to the procedure described by Smith, et al. [Biochem. 9:331-337(1970)]. Ouabain-BSA is linked to Sephadex ®G-25 (Pharmacia, Inc., Piscataway, NJ, USA) after periodate oxidation according to previously described procedures [Wilson, N. and Nakane, P. J. of Immunol. Methods 12, 171–181, (1976)]. The Fab-$\beta$-galactosidase containing sample is passed over a 1×10 cm column of affinity resin. Free $\beta$-galactosidase is eluted from the column and is followed by an eluting solution containing 20 mM ouabain to release the antibody-enzyme conjugate from the column. Five column volumes are washed through and pooled. The pool is concentrated to 2 mL and dialyzed for twenty hours against ten changes of phosphate saline buffer (50 mM sodium phosphate, 0.1M sodium chloride, pH 7.4).

EXAMPLE 2

Preparation of Biotinylated (digoxin)$_n$-Polystyrene Microspheres (a) A suspension (2.5% solids) of amino derivatized polystyrene beads (0.5$\mu$ polybead-amino microspheres, Polysciences, Inc., Warrington, PA, USA) is reacted with sulfosuccinimidyl 6-(biotinamide)hexanoate (Pierce Chemical Co., Rockford, IL, USA) in 0.2M sodium phosphate (pH 7.4) for two hours at 2°-3° C. to incorporate approximately ten biotins per bead. The polystyrene beads are dialyzed against five changes of dialysate buffer containing 0.2M sodium phosphate (pH 7.4).

(b) To prepare a covalently coupled digoxin derivative, 100 mg of digoxin is reacted in 10 mL with a 1:1 molar equivalent of sodium metaperiodate for 30 minutes. A portion of this reagent is then added to the biotinylated beads from (a) and reacted for two hours at room temperature. The Schiff base products of this reaction are then reduced with a two-fold excess of cyanoborohydride and the resulting product is dialyzed against 0.05M sodium phosphate and 0.1M sodium chloride (pH 7.4) with changes of buffer over a period of twelve hours.

EXAMPLE 3

Preparation of Enzyme Detection Reagent Strip and Assembly of Test Device

Whatman 54 filter paper (Whatman Co., Clifton, NJ, USA) is dipped through a solution containing 15 mM substrate, o-nitrophenyl-$\beta$-D-galactose, in 0.3M bicine buffer (pH 7.8) containing 5 mM $MgCl_2$ and dried at 50° C. for fifteen minutes. The dried filter paper containing substrate is laminated onto a double-faced adhesive tape (3M Company, St. Paul, MN, USA) and cut into a 1 cm wide × 12.7 cm long ribbon. The ribbon is then laminated onto and along the length and ¼ inch from the edge of one surface of an 8.3 cm wide × 12.7 cm long clear polystyrene support (Trycite®, Dow Chemical Co., Midland, MI, USA) and slit into 0.5 cm wide × 8.3 cm long reagent strips having the detection layer mounted to the ends thereof.

EXAMPLE 4

Performance of the Assay and Operation of the Test Device (a) To initiate the assay, a 0.25 mL aliquot of anti-digoxin(Fab)-$\beta$-galactosidase conjugate (0.5 nM) in 0.05M bicine (pH 7.6) is added to a 0.05 mL sample of serum containing an unknown amount of digoxin, mixed, and incubated for five (5) minutes at 23° C. A 0.2 mL aliquot of biotinylated(digoxin)$_n$-polystyrene (10% solids) in 0.1M bicine and 0.1M NaCl (pH 7.6) is then added, mixed, and incubated for seven (7) minutes at 23° C. A 0.2 mL aliquot of an avidin solution comprising 30 mg/L avidin (from egg white, Sigma Chemical Co., St. Louis, MO, USA) in 0.1M bicine and 0.1M NaCl (pH 7.8) is added and then incubated for 5 minutes.

(b) A 30 $\mu$l aliquot of the supernatant from (a) is applied to the reagent strip of the test device described in Example 3 above, and the test device is mounted in a reflectance photometer (SERALYZER®, Ames Division, Elkhart, IN, USA) at 37° C. using a 420 nm interference filter to measure the change in reflectance wherein the rate of change is related to the concentration of digoxin in the serum sample.

What is claimed is:

1. In a heterogeneous specific binding assay method for determining the amount of a suspected analyte in an aqueous test medium wherein a reaction mixture is formed by combining the test medium with assay reagents, including a labeled reagent, which results in the formation of free and bound species of the labeled reagent in the reaction mixture as a function of the amount of the analyte in the test medium, wherein one of the free and bound species of the labeled reagent is immobilized, wherein immobilized labeled reagent is separated from labeled reagent which has not been immobilized, and wherein the amount of label in the labeled reagent in one of the separated fractions is determined and related to the amount of analyte in the test medium,
the improvement wherein said one of the free and bound species of the labeled reagent is immobilized by addition of an immobilizable component comprising a water dispersible, aggregatable support material having coupled thereto both (i) a binding partner for the one of said free and bound species to be immobilized and (ii) a first binding substance, and said immobilized labeled reagent is formed by addition of a second binding substance which binds to said first binding substance to cause said support material to aggregate and thereby form a precipitated complex of said support material, wherein said binding partner is different from both said first binding substance and said second binding substance.

2. The method of claim 1 wherein said immobilizable component comprises a water soluble polymer having said binding partner and said first binding substance coupled thereto.

3. The method of claim 2 wherein said second binding substance is in a water soluble form.

4. The method of claim 2 wherein said second binding substance is in a water insoluble form.

5. The method of claim 1 wherein said immobilizable component comprises a water suspensible, insoluble support material having said binding partner and said first binding substance coupled thereto.

6. The method of claim 5 wherein said second binding substance is in a water soluble form.

7. The method of claim 5 wherein said second binding substance is in a water insoluble form.

8. The method of claim 5 wherein said water suspensible, insoluble support material is a polymeric microparticle.

9. The method of claim 8 wherein said polymeric microparticle is a plastic microsphere.

10. The method of claim 1 wherein said first binding substance is biotin or a hapten, and said second binding substance is avidin or an antibody, respectively.

11. The method of claim 1 wherein said binding partner is said analyte or a binding analog or a binding partner thereof.

12. A heterogeneous immunometric assay method for determining the amount of a suspected analyte in an aqueous test medium, said method including the steps of:
(a) forming an aqueous reaction mixture by sequentially combining said aqueous test medium with:
(i) labeled anti-analyte, said labeled anti-analyte being present in said reaction mixture in excess of said suspected analyte and thereby forming free and bound species of said labeled anti-analyte,
(ii) a water dispersible, aggregatable reagent comprising a support material having said analyte or a binding analog thereof and a first binding substance coupled thereto, said analyte or binding analog thereof coupled to the support material being present in said reaction mixture in excess of the free-species form of said labeled anti-analyte, and
(iii) a second binding substance which specifically binds to said first binding substance, said second binding substance aggregating said support material to form a precipitated complex of said support material; and
(b) determining labeled anti-analyte in said precipitated complex or the supernatant as a function of the amount of said suspected analyte in said test medium.

13. The method of claim 12 wherein said support material comprises a water soluble polymer having said analyte or analog and said first binding substance coupled thereto.

14. The method of claim 13 wherein said second binding substance is in a water soluble form.

15. The method of claim 13 wherein said second binding substance is in a water insoluble form.

16. The method of claim 12 wherein said support material comprises a water suspensible, insoluble support material having said analyte or analog and said first binding substance coupled thereto.

17. The method of claim 16 wherein said second binding substance is in a water soluble form.

18. The method of claim 16 wherein said second binding substance is in a water insoluble form.

19. The method of claim 16 wherein said water suspensible, insoluble support material is a polymeric microparticle.

20. The method of claim 19 wherein said polymeric microparticle is a plastic microsphere.

21. The method of claim 12 wherein said reaction mixture is formed by forming a first mixture comprising said aqueous test medium and said labeled anti-analyte, after a predetermined incubation period forming a second mixture comprising said first reaction solution and said water dispersible, aggregatable reagent, and after a predetermined incubation period forming a third mixture comprising said second reaction solution and said second binding substance.

22. The method of claim 12 wherein an aliquot of supernatant is removed from said aqueous reaction mixture without centrifugation and said labeled anti-analyte determined therein.

23. The method of claim 12 wherein said labeled anti-analyte is a labeled monovalent antibody fragment.

24. The method of claim 12 wherein said anti-analyte is labeled with an enzyme and wherein the enzyme activity of said enzyme-labeled anti-analyte resulting in the precipitated complex or the supernatant is proportional to the amount of analyte in said aqueous test medium.

25. The method of claim 12 wherein said first binding substance is biotin or a hapten, and said second binding substance is avidin or an antibody, respectively.

26. A test kit for a heterogeneous immunometric assay for determining the amount of suspected analyte in an aqueous test medium, said test kit comprising:
    (a) labeled anti-analyte,
    (b) a water dispersible, aggregatable reagent comprising a support material having said analyte or a binding analog thereof and a first binding substance coupled thereto, and
    (c) a second binding substance capable of specifically binding to said first binding substance to form a precipitated complex of said support material.

27. The test kit of claim 26 wherein said support material comprises a water soluble polymer having said analyte or analog and said first binding substance coupled thereto.

28. The test kit of claim 27 wherein said second binding substance is in a water soluble form.

29. The test kit of claim 27 wherein said second binding substance is in a water insoluble form.

30. The test kit of claim 26 wherein said support material comprises a water suspensible and insoluble support material having said analyte or analog and said first binding substance coupled thereto.

31. The test kit of claim 30 wherein said second binding substance is in a water soluble form.

32. The test kit of claim 30 wherein said second binding substance is in a water insoluble form.

33. The test kit of claim 30 wherein said water suspensible, insoluble support material is a polymeric microparticle.

34. The test kit of claim 33 wherein said polymeric microparticle is a plastic microsphere.

35. The test kit of claim 26 wherein said labeled anti-analyte is a labeled monovalent antibody fragment.

36. The test kit of claim 26 wherein said anti-analyte is labeled with an enzyme.

37. The test kit of claim 36 which further includes an indicator which provides a color change in response to the activity of said enzyme.

38. The test kit of claim 37 wherein said indicator is incorporated within a solid carrier matrix in the form of a test strip.

39. The test kit of claim 26 wherein said first binding substance is biotin or a hapten, and said second binding substance is avidin or an antibody respectively.

* * * * *